(12) United States Patent
Sheldon (10) Patent No.: US 9,079,178 B2
(45) Date of Patent: Jul. 14, 2015

(54) APPARATUS AND METHODS FOR PIPETTING WITH INTERCHANGEABILITY AMONG DIFFERENT PIPETTE TIPS

(71) Applicant: AGILENT TECHNOLOGIES, INC., Loveland, CO (US)

(72) Inventor: Brian M. Sheldon, Katonah, NY (US)

(73) Assignee: Agilent Technologies, Inc., Santa Clara, CA (US)

( * ) Notice: Subject to any disclaimer, the term of this patent is extended or adjusted under 35 U.S.C. 154(b) by 183 days.

(21) Appl. No.: 13/760,697

(22) Filed: Feb. 6, 2013

(65) Prior Publication Data

US 2014/0219887 A1  Aug. 7, 2014

(51) Int. Cl.
*B01L 3/02* (2006.01)
*G01N 35/10* (2006.01)

(52) U.S. Cl.
CPC .......... *B01L 3/0279* (2013.01); *G01N 35/1016* (2013.01); *B01L 2200/023* (2013.01); *G01N 2035/103* (2013.01); *Y10T 29/49826* (2015.01)

(58) Field of Classification Search
CPC .............................................. B01L 2200/023
USPC .......................... 422/509, 511, 516, 524–526; 73/864.01–864.25
See application file for complete search history.

(56) References Cited

U.S. PATENT DOCUMENTS

| | | | |
|---|---|---|---|
| 5,906,795 A | 5/1999 | Nakashima et al. | |
| 6,090,348 A * | 7/2000 | Steele et al. | 422/67 |
| 2004/0071602 A1 * | 4/2004 | Yiu | 422/100 |
| 2006/0177345 A1 | 8/2006 | Fritz et al. | |
| 2010/0247378 A1 * | 9/2010 | Cerra et al. | 422/67 |
| 2013/0068041 A1 * | 3/2013 | Naumann et al. | 73/864.01 |
| 2014/0051182 A1 * | 2/2014 | Reichmuth et al. | 436/180 |

* cited by examiner

*Primary Examiner* — Jan Ludlow (57) ABSTRACT

Pipette tips of different sizes may be coupled to a pipettor without needing to modify the pipettor. The same pipettor may thus be utilized to exchange different pipette tips, which may be done in an automated manner. Pipette tips may be coupled to adaptors that include proximal ends for interfacing with the pipettor and distal ends for interfacing with pipette tips. The proximal ends may all have the same geometry, matched with the same pipettor. The distal ends may have different geometries matched with different pipette tips. A pipettor may be part of a liquid handling apparatus and movable in an automated manner to different deck positions. The pipettor may include a locking mechanism for locking adaptors to the pipettor or locking pipette tips directly to the pipettors, and an ejection mechanism for ejecting pipette tips from corresponding adaptors.

13 Claims, 8 Drawing Sheets

APPARATUS AND METHODS FOR PIPETTING WITH INTERCHANGEABILITY AMONG DIFFERENT PIPETTE TIPS

TECHNICAL FIELD

The present invention relates generally to pipetting. More particularly, the invention relates to automated pipetting in which different pipette tips are compatible with the same pipetting apparatus.

BACKGROUND

A wide variety of liquid handling apparatuses and pipettors are available and are capable of a wide variety of liquid handling functions, as appreciated by persons skilled in the art. Generally, a pipettor is utilized for aspirating and dispensing precise volumes of liquid, typically by air displacement. The pipettor includes a syringe coupled with a pipette tip. The syringe includes a piston that moves through a barrel. The pipette tip is coupled to the syringe such that an air path is established between the barrel and the pipette tip. The piston is driven manually or by a motor to alternately execute a forward stroke and backward stroke in the barrel. The forward stroke increases air pressure and thus can be utilized to dispense liquid from the pipette tip. The backward stroke creates suction and thus can be utilized to aspirate liquid into the pipette tip. One or more pipettors may be included in an automated pipetting device, which may be part of a liquid handling apparatus that utilizes liquid containers such as multi-well plates. The pipetting device may be movable to and from different multi-well plates located on a deck of the liquid handling apparatus. Thus, for instance, the pipettors may be operated to aspirate desired amounts of liquid from one multi-well plate into the pipette tips coupled to the pipettors, transport the liquid held in the pipette tips to another multi-well plate, and dispense the liquid from the pipette tips into desired wells of that other multi-well plate.

Pipette tips are available in many different sizes (e.g., 10 μL, 50 μL, 300 μL, 1 mL, 5 mL, etc.) and geometries, including both disposable and non-disposable types. Different procedures or protocols may require different pipette tips (in terms of size and/or type), and in some cases the same procedure or protocol may require the use of different pipette tips. Some existing pipetting devices have the ability to accommodate different styles of pipette tips, but require a user to manually change pipette tips between automated procedures or protocols. Some existing pipetting devices have the ability to automatically change disposable tips and non-disposable tips during a procedure or protocol, but require the ends of those tips (which are to be coupled to the syringes) to have the same interface geometry. To accommodate disposable tips sized to hold large volumes (e.g., 1000 μL), the interface geometry is designed around those large tips. Thus, smaller volume disposable tips (e.g., 10 μL) must use the same interface to the pipettor as is used by the much larger tips, resulting for instance in a smaller volume tip that is not optimally designed for its small volume and use or application. For example, the interface of the smaller volume tip is much larger than desired. Moreover, because the interface on the smaller volume tips is forced to be large (again, to be interchangeable with larger volume tips in conjunction with the same pipettor), the smaller volume tips cannot be placed in a grid next to each other at the relatively small spacing (e.g., 4.5 mm) required to access the adjacent wells of a multi-well (e.g., 384 well) plate of standard size. In addition, different procedures or protocols may require the use of multi-channel pipetting devices and/or single-channel pipetting devices. These two types of pipetting devices often have different interfaces, and thus the same size or type of pipette tip may not be usable on both a multi-channel pipetting devices and a single-channel pipetting devices.

Generally, there is an ongoing need for increasing the level of automation provided by liquid handling and pipetting instruments to increase throughput and the "walk away" time afforded to users of such instruments. In particular, there is a need for increasing the level of interchangeability among different types and sizes of pipette tips, and for automating the tasks of coupling pipette tips to syringes, decoupling pipette tips from syringes, and exchanging different pipette tips in an automated manner.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one embodiment, a method for operating a pipettor includes: selecting a first pipette tip from a plurality of pipette tips, the plurality of pipette tips including one or more of the first pipette tips and one or more second pipette tips, wherein the first pipette tip includes a first pipette tip proximal end of a first interface geometry and the second pipette tip includes a second pipette tip proximal end of a second interface geometry different from the first interface geometry; selecting a first adaptor from a plurality of hollow adaptors, the plurality of adaptors including one or more of the first adaptors and one or more second adaptors, wherein the first adaptor includes a first adaptor proximal end and a first adaptor distal end, the first adaptor distal end is configured for interfacing with the first pipette tip proximal end, the second adaptor includes a second adaptor proximal end of a same interface geometry as the first adaptor proximal end and a second adaptor distal end of a different interface geometry than the first adaptor distal end, and the second adaptor distal end is configured for interfacing with the second pipette tip proximal end; moving the pipettor to the selected first adaptor; fluidly coupling the pipettor with the first adaptor; moving the pipettor with the first adaptor to the selected first pipette tip; and fluidly coupling the first adaptor with the first pipette tip.

According to another embodiment, a kit for a pipettor includes: a plurality of hollow adaptors including one or more first adaptors and one or more second adaptors, wherein: the first adaptor includes a first adaptor proximal end and a first adaptor distal end, the first adaptor proximal end is configured for interfacing with a pipettor, and the first adaptor distal end is configured for interfacing with a first pipette tip; and the second adaptor includes a second adaptor proximal end having the same interface geometry as the first adaptor proximal end and a second adaptor distal end having a different interface geometry than the first adaptor distal end, the second adaptor proximal end is configured for interfacing with the pipettor, and the second adaptor distal end is configured for interfacing with a second pipette tip of a different size than the first pipette tip.

According to another embodiment, a liquid handling apparatus includes: a deck; a pipette tip holder disposed on the deck and configured for holding pipette tips; an adaptor holder disposed on the deck and configured for holding the first adaptors; the second adaptors, or both the first adaptors and the second adaptors; and a pipettor movable to the first pipette tip holder and to the second pipette tip holder, and configured for fluidly coupling with a selected one of the first adaptors and second adaptors.

According to another embodiment, a pipettor includes: a housing; a barrel disposed in the housing; a motor-driven piston alternately movable along a forward stroke and a backward stroke in the barrel; a receptacle communicating with the barrel and configured for fluidly coupling with an adaptor; and a locking mechanism configured for releasably locking the adaptor into engagement with the receptacle.

According to another embodiment, the pipettor includes an ejection mechanism configured for ejecting a pipette tip from the adaptor to which the pipette tip is coupled.

According to another embodiment, a pipetting device includes: a plurality of pipettors, each pipettor comprising a barrel, a piston, and a plurality of receptacles communicating with the respective barrels; and a motor communicating with the pipettors, wherein the motor is a single motor configured for moving the pipettors simultaneously, or a plurality of motors configured for motors the respective pipettors independently Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION

Figure 1:
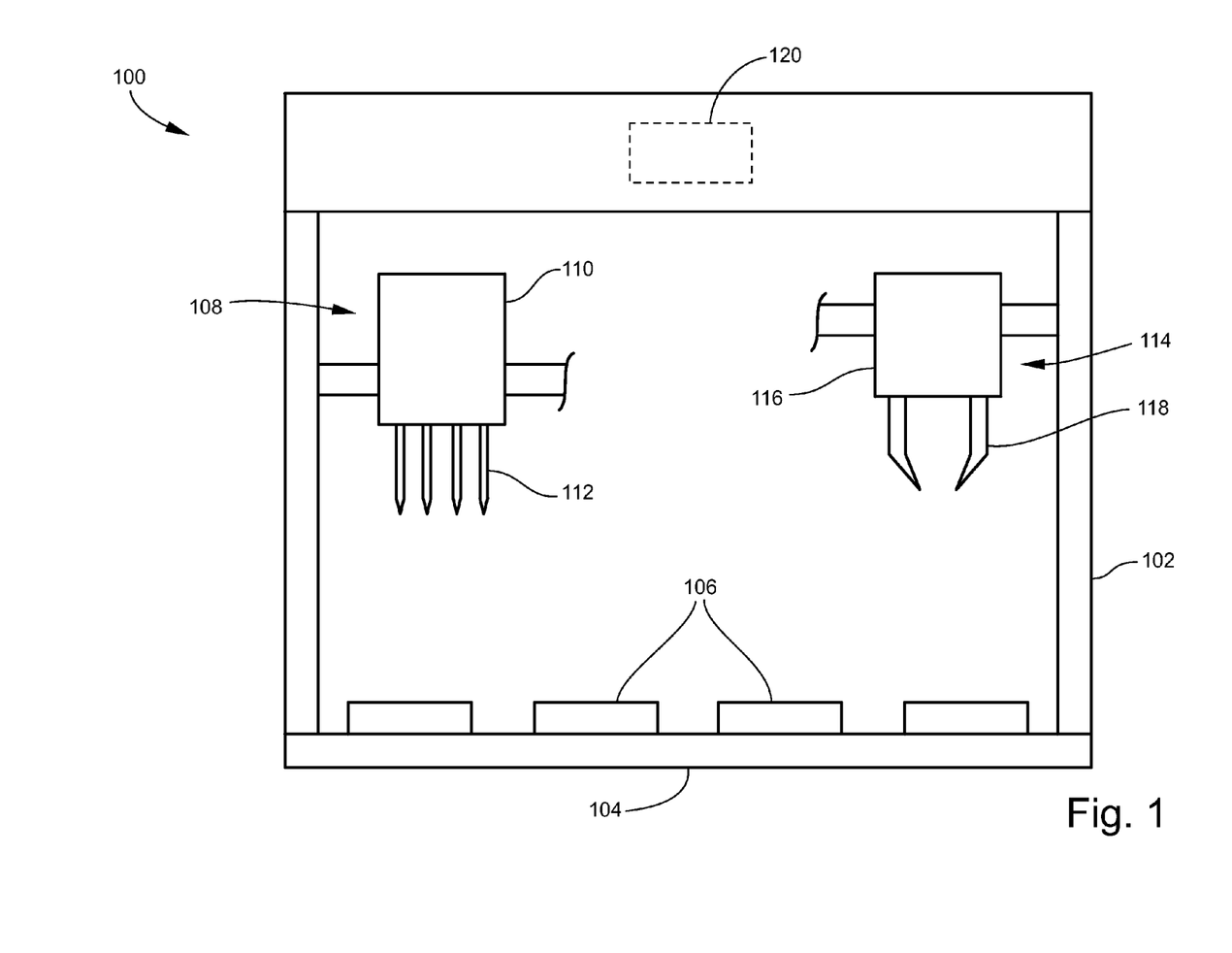
FIG. 1 is a schematic front elevation view of an example of an automated liquid handling apparatus or system according to some embodiments.

FIG. 1 is a schematic front elevation view of an example of an automated liquid handling apparatus or system 100 according to some embodiments. Generally, the liquid handling apparatus 100 may be utilized in conjunction with any high-throughput method or protocol entailing the handling of liquids in fields such as, for example, analytical separation, isolation or purification, genomics, proteomics, cell biology, screening/assaying, toxicology, pharmacology, sample preparation, etc. The liquid handling apparatus 100 may include a structural frame or housing 102 that supports or contains various components. The frame 102 may include a deck 104 providing a plurality of deck sites or stations at which various functional deck components 106 may be located. The deck components 106 may be arranged in a two-dimensional array on the deck 104. The deck components 106 may include, for example, holders for multi-well plates of standard format (96-well, 384-well, etc.), holders for disposable pipette tips, holders for re-usable ("fixed") pipette tips, holders or racks for other types of liquid containers (tubes, vials, cuvettes, etc.), holders for adaptors (described further below), holders for other types of instrumentation or labware, rinse stations, heating stations, agitating/shaking stations, vacuum filtration stations, weigh stations, reservoirs for liquids (e.g., solvents, buffers, reagents, markers/labels, etc.), stations for carrying out measurements, assays, analyses, purification, or sample preparation, etc. As used herein, the term "liquid container" generally encompasses any device for holding one or more quantities of liquid, and thus encompasses multi-well plates (or microtiter plates, or microplates) as well as tubes, vials, cuvettes or the like and associated holders thereof.

The liquid handling apparatus 100 may further include a pipetting device or assembly 108. The pipetting device 108 may include a housing or head 110 mounted on one or more gantries or stages such that the head 110 is movable in two or three dimensions (x-y-z axes). The head 110 may include a plurality of pipettors, which typically are syringe-based. Thus, the pipettors may include respective syringes that may be fluidly coupled to a plurality of pipette tips 112. Each syringe may include a motor-driven piston that reciprocates in a syringe barrel, as appreciated by persons skilled in the art. The pipetting device 108 is movable to the various deck sites. At any selected deck site, the pipetting device 108 may be operated to dispense liquid from one or more of the pipette tips 112 to one or more components 106 at the deck site or aspirate liquid from one or more components 106 into one or more pipette tips 112. In some embodiments, the pipetting device 108 is a multi-channel device that dispenses liquid from (or aspirates liquid into) each pipette tip 112 simultaneously. For example, the pipetting device 108 may include an array of 96 pipette tips 112 utilized in conjunction with a 96-well plate located at a deck site, and liquid transfer occurs at all 96 wells simultaneously. In this case, a single motor may drive all pistons simultaneously through an appropriate linkage. In other embodiments, the pipetting device 108 may consist of one or more single channel pipettors capable of controlling liquid transfer to or from each pipette tip 112 individually. In this case, each individual pipettor may include an independent motor for driving the associated syringe piston. Also, each individual pipettor may include independent motor drives for moving the pipettor in two or more directions. Such freedom of movement may be useful, for example, for enabling variable pipettor spacing.

The liquid handling apparatus 100 may further include a robot 114. The robot 114 may include a head 116 mounted on a gantry or stage that is movable in two or three dimensions (x-y-z axes). The robot 114 may further include a gripper 118 configured for securely gripping various components 106 on the deck 104 and transporting the components 106 to other locations on the deck 104, or to other modules external to the liquid handling apparatus 100, such as another liquid handling apparatus or an analytical instrument (e.g., a chromatograph, a mass spectrometer, etc.). The robot 114 may also include one or more robotic arms (not shown) interconnecting the gripper 118 and the head 116 and capable of motion in one or more directions. The arm(s) may be provided to extend the reach of the gripper 118 to locations external to the deck 104.

The liquid handling apparatus 100 may further include a controller 120. In FIG. 1, the controller 120 is shown at an arbitrary location associated with the frame or housing 102. The controller 120 may, however, be located at an external or remote location relative to the liquid handling apparatus 100. The controller 120 is schematically depicted as representing one or more modules configured for controlling, monitoring and/or timing various functional aspects of the liquid handling apparatus 100 such as, for example, the operations of the pipettor 108 and robot 114. The controller 120 may include a computer-readable medium that includes instructions for performing all or part of any of the methods disclosed herein. For all such purposes, the controller 120 may be placed in signal communication with various components of the liquid handling apparatus 100 via wired or wireless communication links, as appreciated by persons skilled in the art. Also for these purposes, the controller 120 may include one or more types of hardware, firmware and/or software, as well as one or more memories and databases. The controller 120 typically includes a main electronic processor providing overall control, and may include one or more electronic processors configured for dedicated control operations or specific signal processing tasks. The controller 120 may also be representative of one or more types of user interface devices, such as user input devices (e.g., keypad, touch screen, mouse, and the like), user output devices (e.g., display screen, printer, visual indicators or alerts, audible indicators or alerts, and the like), a graphical user interface (GUI) controlled by software, and devices for loading media readable by the electronic processor (e.g., logic instructions embodied in software, data, and the like). The controller 120 may include an operating system (e.g., Microsoft Windows® software) for controlling and managing various functions of the controller 120.

It will be understood that FIG. 1 is a high-level schematic depiction of the liquid handling apparatus 100 disclosed herein. Other components may be included as needed for practical implementations, as appreciated by persons skilled in the art.

Figure 2:
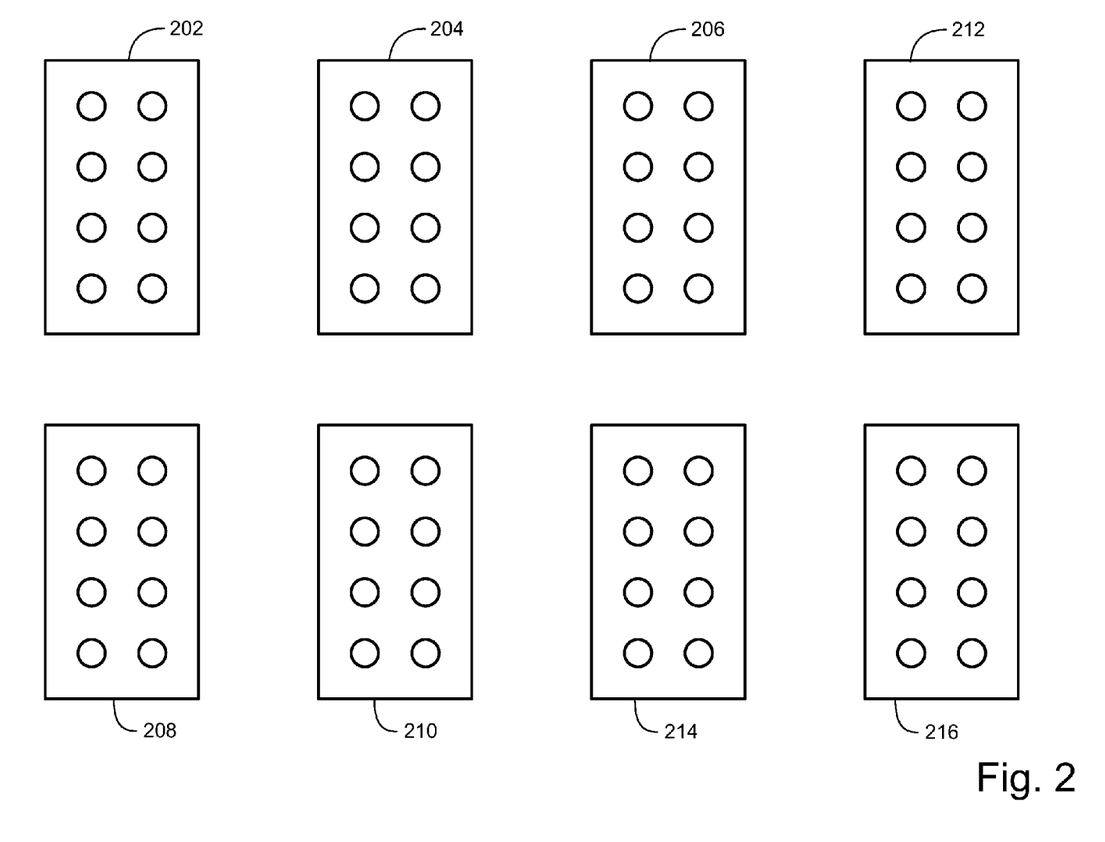
FIG. 2 is a schematic top plan view of an example of a layout of components on a deck of a liquid handling apparatus according to some embodiments.

FIG. 2 is a schematic top plan view of an example of a layout of components on the deck 104 of the liquid handling apparatus 100. In the illustrated example, the components include a first pipette tip holder 202, a second pipette tip holder 204, a third pipette tip holder 206, a first adaptor holder 208, a second adaptor holder 210, and multi-well plates 212, 214 and 216 of the same format or different formats (or other types of liquid containers). The first pipette tip holder 202 may be configured for holding pipette tips of a first size (first pipette tips), the second pipette tip holder 204 may be configured for holding pipette tips of a second size (second pipette tips), and the third pipette tip holder 206 may be configured holding for pipette tips of a third size (third pipette tips). Alternatively, one or more of the pipette tip holders 202, 204 and 206 may be configured for holding pipette tips of different sizes. Likewise, the first adaptor holder 208 may be configured for holding adaptors of a first size (first adaptors) and the second adaptor holder 210 may be configured for holding adaptors of a second size (second adaptors), or one or more of the adaptor holders 208 and 210 may be configured for holding adaptors of different sizes. Each holder 202-210 may include a plurality of apertures 218 or equivalent features for holding a like number of pipetting components (pipette tips or adaptors) in a one-dimensional or two-dimensional array in a repeatable manner with consistent, uniform spacing between the pipetting components. Some of the pipette tips may be disposable pipette tips, which are typically composed of an inert polymer but may alternatively be composed of a metal or ceramic. Other pipette tips may be "reusable" (or "fixed" or "non-disposable") pipette tips, which are reusable after appropriate rinsing or sterilization. Resuable pipette tips are typically composed of a metal but may alternatively be composed of a polymer or ceramic. The adaptors are usable with disposable pipette tips, as described below. As used herein the term "disposable pipette tips" generally refers to pipette tips that may be coupled to, and thereafter decoupled from, adaptors. As described below, a disposable pipette tip (e.g., first or second pipette tip) may be fluidly coupled to a syringe indirectly by utilizing an adaptor (e.g., a first adaptor or second adaptor), whereas a reusable tip (e.g., third pipette tip) may be fluidly coupled to a syringe directly without utilizing an adaptor.

It will be understood that the number of deck components illustrated in FIG. 2 is by example only. Any number of rows and columns of the components, and any number of components in a given row or column, may be provided. Moreover, additional holders may be provided for storing pipette tips or adaptors of additional different sizes, and additional multi-well plates or other containers may be provided. Moreover, other types of components such as those noted above may be provided on the deck 104.

Figure 3:
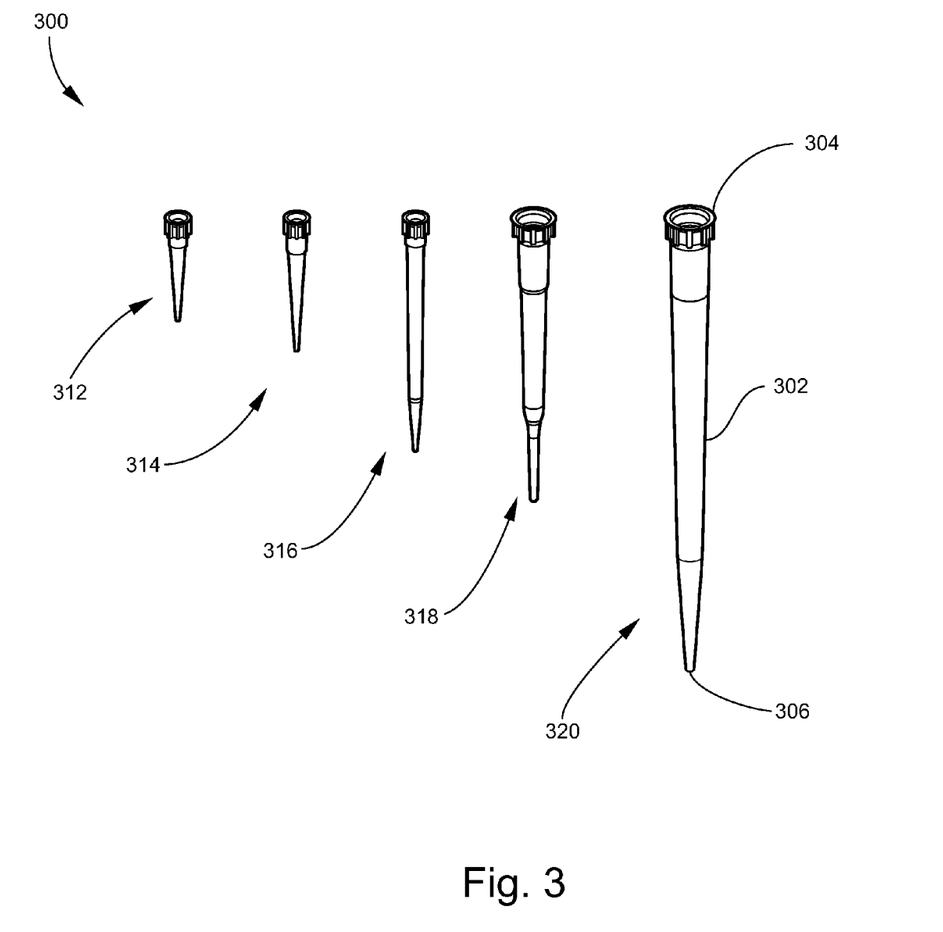
FIG. 3 is a slightly perspective view of an example of a set of disposable pipette tips that may be utilized in accordance with the present teachings.

FIG. 3 is a slightly perspective view of an example of a set 300 of disposable pipette tips 312-320 that may be utilized in conjunction with the present teachings. Each pipette tip generally includes a hollow pipette body 302 elongated between an open pipette tip proximal end 304 and an axially opposing open pipette tip distal end 306. All or a portion of the pipette body 302 may be tapered (i.e., have a varying inside diameter). Thus in the illustrated example, the inside diameter of the pipette tip distal end 306 is less than the inside diameter of the pipette tip proximal end 304. The internal dimensions of the pipette body 302 define the volumetric capacity of the pipette tip. The five pipette tips illustrated in FIG. 3 are of different sizes, meaning they are configured to hold different volumes of liquid. By example, going from left to right in FIG. 3, the first pipette tip 312 has a size (or volume) of 10 μL, the second pipette tip 314 has a size of 30 μL, the third pipette tip 316 has a size of 70 μL, the fourth pipette tip 318 has a size of 250 μL, and the fifth pipette tip 320 has a size of 1000 μL. The respective "sizes" or "volumes" of the pipette tips may be dictated by their axial lengths and/or their inside diameters, e.g., the inside diameters at their respective proximal ends 304. Thus, in the illustrated example, the inside diameters of the proximal ends of the first pipette tip 312, second pipette tip 314, and third pipette tip 316 are the same but their axial lengths are successively greater. The inside diameter of the proximal end of the fourth pipette tip 318 is greater than that of the first pipette tip 312, second pipette tip 314, and third pipette tip 316, but is less than that of the fifth pipette tip 320. The axial length of the fourth pipette tip 318 is greater than those of the first pipette tip 312, second pipette tip 314, and third pipette tip 316, but is less than that of the fifth pipette tip 320.

As shown in FIG. 3, the geometries (i.e., the size and shape of features, such as for example inside diameter) of the first pipette tip 312, second pipette tip 314, and third pipette tip 316 at their proximal ends are the same. This means that the first pipette tip 312, second pipette tip 314, and third pipette tip 316 may be fluidly coupled with the syringe of a pipettor in the same manner. In other words, the first pipette tip 312, second pipette tip 314, and third pipette tip 316 are all compatible with the same structural interface of a given pipettor. Consequently, a single pipettor may be utilized, without manual modification, to exchange different sizes of pipette tips, so long as the different pipette tips have the same interface geometry as in the case of the first pipette tip 312, second pipette tip 314, and third pipette tip 316 shown in FIG. 3. However, the interface geometries of the fourth pipette tip 318 and fifth pipette tip 320 are different from each other and from the first pipette tip 312, second pipette tip 314, and third pipette tip 316. Therefore, neither the fourth pipette tip 318 nor the fifth pipette tip 320 is interchangeable with the first pipette tip 312, second pipette tip 314, or third pipette tip 316, and the fourth pipette tip 318 and fifth pipette tip 320 are not interchangeable with each other, unless the pipettor or a portion thereof is manually modified or replaced with a different pipettor or a portion thereof.

Figure 4:
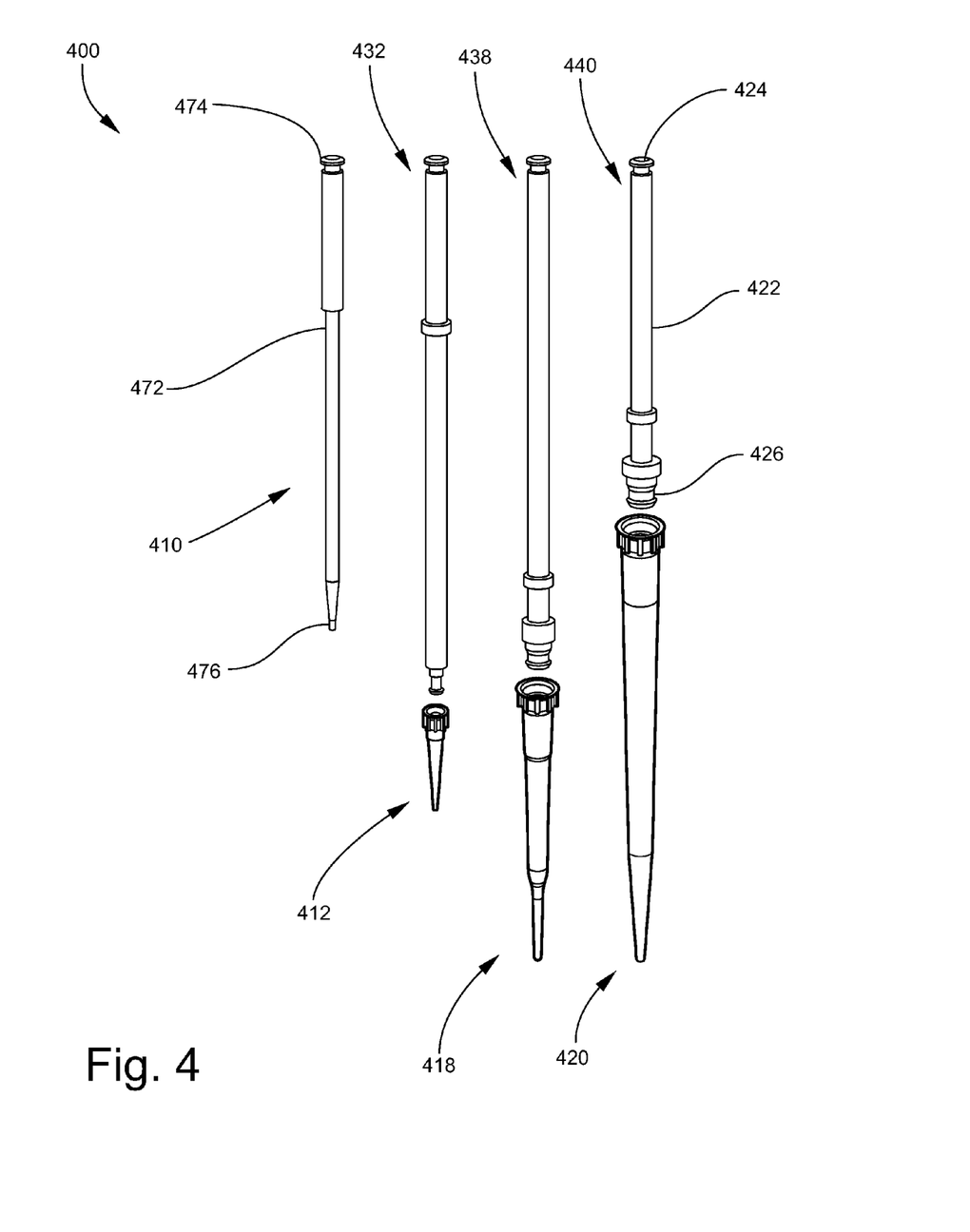
FIG. 4 is a slightly perspective view of an example of a set of adaptors and corresponding pipette tips, along with one example of a fixed pipette tip, which may be utilized in accordance with the present teachings.

The above noted problem may be remedied by an aspect of the present teachings illustrated in FIG. 4. FIG. 4 is a slightly perspective view of an example of a set 400 of adaptors 432, 438 and 440 and corresponding pipette tips 412, 418 and 420, along with one example of a reusable pipette tip 410. Each adaptor generally includes a hollow adaptor body 422 elongated between an open adaptor proximal end 424 and an axially opposing open adaptor distal end 426. The adaptor proximal end 424 is configured for fluid coupling with a syringe of a pipettor, and the adaptor distal end 426 is configured for fluid coupling with the proximal end of a corresponding pipette tip.

As shown in FIG. 4, the proximal ends 424 of the adaptors 432, 438 and 440 all have the same interface geometry. In the present context, the term "interface geometry" generally refers to the overall shape (or profile) and/or overall size of the proximal end 424. By having the same interface geometry at the proximal end 424, each adaptor 432, 438 and 440 may be interfaced with the same pipettor. Stated in another way, each adaptor 432, 438 and 440 is configured for interfacing with the same pipettor. In the present context, "configured for interfacing" means that the interface geometry of each adaptor 432, 438 and 440 is compatible with, matched with, or complementary to the interface geometry of the portion of the syringe that receives the proximal end 424 so as to be able to form a fluid coupling suitable for pipetting operations (e.g., maintaining an air path between the syringe and the adaptor). In some embodiments, two or more proximal ends 424 having the same interface geometry may also have the same diameter. However, two or more proximal ends 424 can have the same interface geometry, and thus be configured for interfacing with the same pipettor, while having slightly different diameters. More generally, two or more proximal ends 424 can have the same interface geometry even though a certain feature (e.g., inside diameter, outside diameter, a surface portion or other structural feature) of their respective interface geometries differs or varies slightly.

As also shown in FIG. 4, however, the respective distal ends 426 of the three adaptors 432, 438 and 440 have different interface geometries. Consequently, the three adaptors 432, 438 and 440 are configured for interfacing with different (e.g., differently sized) pipette tips 412, 418 and 420. Specifically, the first adaptor 432 is configured for interfacing with a first pipette tip 412, which may correspond to the first pipette tip, second pipette tip or third pipette tip described above and illustrated in FIG. 3. In the present context, "configured for interfacing" means that the interface geometry of the distal end of the first adaptor 432 is compatible with, matched with, or complementary to the interface geometry of the proximal end of the first pipette tip 412 so as to be able to form a fluid coupling suitable for pipetting operations (e.g., maintaining an air path between the first adaptor 432 and the first pipette tip 412). The first adaptor 432 may be fluidly coupled to the first pipette tip 412 by, for example, secure contact between the adaptor distal end and the pipette tip proximal end. In some embodiments, secure contact entails a press fit (i.e., a friction fit or interference fit) between the adaptor distal end and the pipette tip proximal end. Likewise, the second adaptor 438 is configured for interfacing with a second pipette tip 418, which may correspond to the fourth pipette tip of FIG. 3, and the third adaptor 440 is configured for interfacing with a third pipette tip 420, which may correspond to the fifth pipette tip of FIG. 3.

In some typical embodiments such as illustrated in FIG. 4, the distal end of the first adaptor 432 is the smallest and is matched with the smallest pipette tip, the distal end of the second adaptor 438 is larger than that of the first adaptor 432 and is matched with a larger pipette tip, and the distal end of the third adaptor 440 is larger than that of the second adaptor 438 and is matched with an even larger pipette tip. More generally, however, as indicated above the sameness or difference between the interface geometries of the distal ends of two or more adaptors is not necessarily dictated by the size or dimension of any one specific feature of the distal ends. The distal ends of two adaptors may have some differences yet both distal ends have the same interface geometry because both distal ends can be fluidly coupled to a pipette tip of a specific size (or type) and cannot be fluidly coupled to a pipette tip of a different size (or type).

By coupling an adaptor between a pipette tip and the syringe of a pipettor, the same pipettor (and the same syringe interface thereof) may be utilized with pipette tips of any size. Each adaptor has an interface geometry matched with a pipette tip of a specific size, and all adaptors have an interface geometry matched with the same pipettor. Hence, the adaptor provides differently sized pipette tips with the same coupling interface to the pipettor, thereby enabling differently sized pipette tips to be readily exchanged without needing to manually modify or replace the pipettor. This in turn enables the various dimensions and geometric features of pipette tips to be optimized or tailored to their specific volumes. That is, a pipette tip of a given volume may be sized or configured without having to consider or accommodate the size or configuration of a pipette tip of a different volume. For instance, due to the provision of adaptors, the interface geometry of the proximal end of the first pipette tip 312 shown in FIG. 3 can be kept small in comparison to, for example, the fourth pipette tip 318 and fifth pipette tip 320 shown in FIG. 3. This, for example, enables the first pipette tip 312 to have an axial length and inside diameter appropriate for its small volume, and facilitates grouping a plurality of first pipette tips 312 in a closely spaced array that conforms to the array of wells of a standard-format plate (e.g., a 384-well plate).

Figure 5:
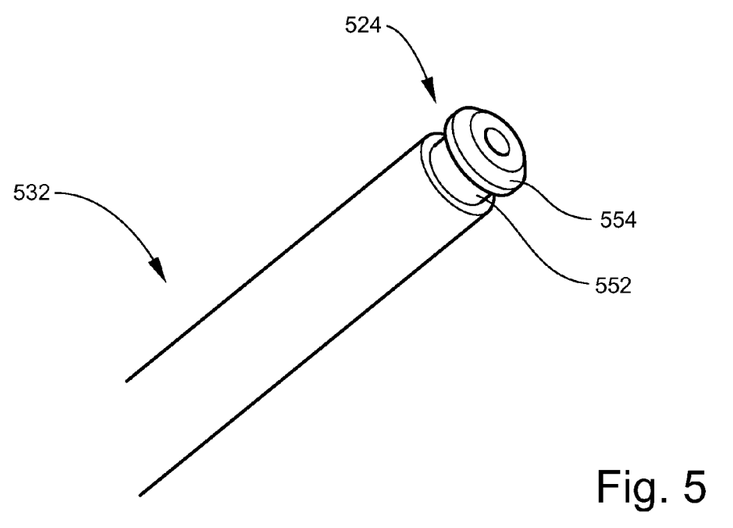
FIG. 5 is a perspective view of an example of a proximal end of an adaptor according to some embodiments.

FIG. 5 is a perspective view of an example of a proximal end 524 of an adaptor 532. In this example, the interface geometry of the proximal end 524 includes a circumferential groove or slot 552, which may be utilized to create a secure fluid coupling between the adaptor 532 and the syringe of a pipettor in a manner described below. The proximal end 524 may also include a beveled circumferential top edge 554 to assist in aligning the proximal end 524 with the syringe during the interfacing process.

Figure 6:
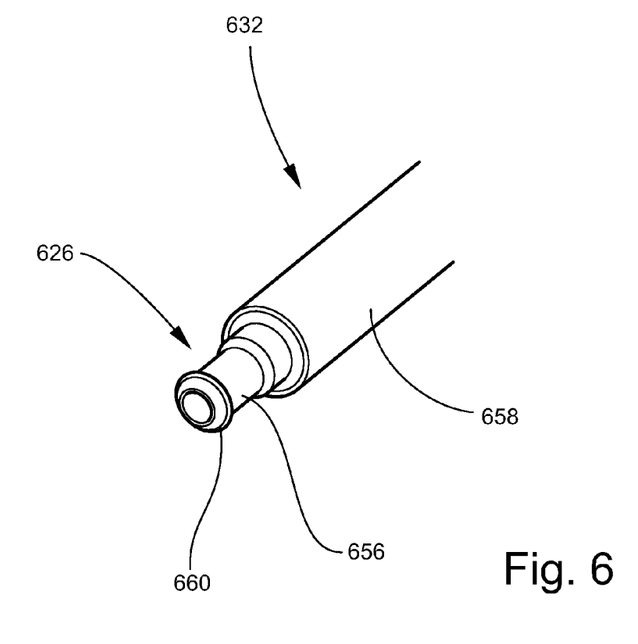
FIG. 6 is a perspective view of an example of a distal end of an adaptor according to some embodiments.

FIG. 6 is a perspective view of an example of a distal end 626 of an adaptor 632. In this example, the interface geometry of the distal end 626 includes a reduced diameter section 656 having an outside diameter less than that of a main body 658 of the adaptor 632. The distal end 626 may also include one or more protrusions 660, such as an annular rib, extending in a radial direction outward from the reduced diameter section 656. The adaptor distal end 626, including the reduced diameter section 656 and protrusion 660, is sized to fit inside the proximal end of a corresponding pipette tip. The adaptor distal end 626 may be inserted into the pipette tip proximal end until an outside surface of the adaptor distal end 626 (e.g., the protrusion 660) comes into contact with an inside surface of the pipette tip proximal end. A small force may be imparted to secure the interface, i.e., the adaptor 632 may be fluidly coupled with the pipette tip in a secure manner by, for example, press fitting. The adaptor 632 may thereafter be decoupled from the pipette tip using a small pulling force. In other embodiments, the outside diameter of the pipette tip proximal end may be smaller than the inside diameter of the adaptor distal end 626, such that the pipette tip proximal end fits inside the adaptor distal end 626.

As also shown in FIG. 4, the respective axial lengths of the adaptors 432, 438 and 440 may be different to accommodate different axial lengths of the corresponding pipette tips 412, 418 and 420 as needed or desired. Longer adaptors may be utilized with shorter pipette tips, and shorter adaptors may be utilized with longer pipette tips. Depending on the embodiment, the overall length of each combination of adaptor and pipette tip may or may not need to be uniform. The axial length of an adaptor does not raise an issue of "dead liquid volume" that might adversely affect pipetting performance. The syringe of the pipettor may be operated such that liquid is always contained solely in the pipette tip and is not aspirated into the interior of the adaptor. In such a case, the adaptor provides an extension of the air path associated with the syringe barrel and is not utilized to hold or transport liquid. However, it may be desirable to minimize "dead air volume" to minimize the compliance of the air circuit and thereby enhance the precision of aspiration and dispensing operations. Thus, the diameter of the internal bore of the adaptor may be kept as small as possible to minimize the volume of the air path through the adaptor.

Figure 7:
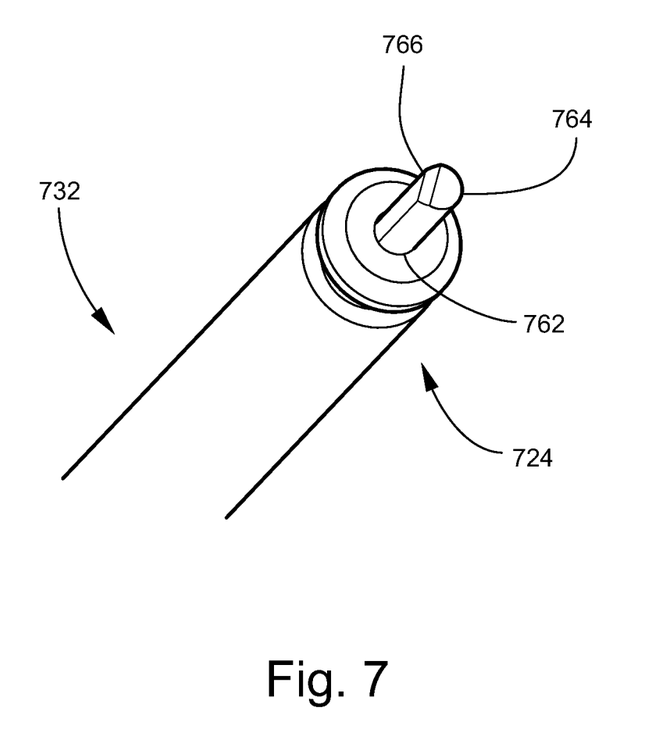
FIG. 7 is a perspective view of an example of a proximal end of an adaptor, with a rod inserted into an internal bore of the adaptor according to some embodiments.

The adaptor generally may be composed of any metal, polymer or ceramic, and may be fabricated by any suitable technique. As noted above, in typical embodiments the adaptor provides an air path between the syringe and the pipette tip and does not hold or transport liquid. Moreover, the internal bore of the adaptor may have a small diameter. Formation of the internal bore may depend on the composition of the adaptor and the fabrication technique utilized. The bore may be formed, for example, by mechanical drilling, ultrasonic drilling, laser drilling, wet (e.g., chemical) etching, dry (e.g., plasma or ion) etching, or molding around a removable core pin. Another example is illustrated in FIG. 7, which is a perspective view of an example of a proximal end 724 of an adaptor 732. In this embodiment, a bore 762 of relatively large diameter has been initially drilled through the axial length of the adaptor 732. A rod 764 is then inserted into the bore 762. One or more sides of the rod 764 have a flat face 766, such that a space is established between the flat face 766 and the inside surface of the bore 762. Thus, insertion of the rod 764 into the bore 762 in effect reduces the cross-sectional area of the bore 762 to a smaller size sufficient for providing an air path through the adaptor 732. Alternatively, the rod 764 may have one or more longitudinal grooves or recesses; for example, the rod 764 may be fluted.

FIG. 4 also illustrates one example of a fixed or reusable pipette tip 410. This type of pipette tip is intended to be reusable and thus is typically composed of a metal but may alternatively be composed of a polymer or ceramic. One or more reusable pipette tips of different sizes may be provided. Each reusable pipette tip 410 generally includes a hollow pipette body 472 elongated between an open pipette tip proximal end 474 and an axially opposing open pipette tip distal end 476. All or a portion of the pipette body 472 may be tapered. Thus in the illustrated example, the inside diameter of the pipette tip distal end 476 is less than the inside diameter of the pipette tip proximal end 474. In use, the reusable pipette tip 410 is coupled directly to the syringe, without employing an adaptor. For this purpose, the proximal end 474 of each reusable pipette tip 410 has the same interface geometry as the proximal ends 424 of the adaptors 432, 438 and 440, as shown in FIG. 4.

Figure 8:
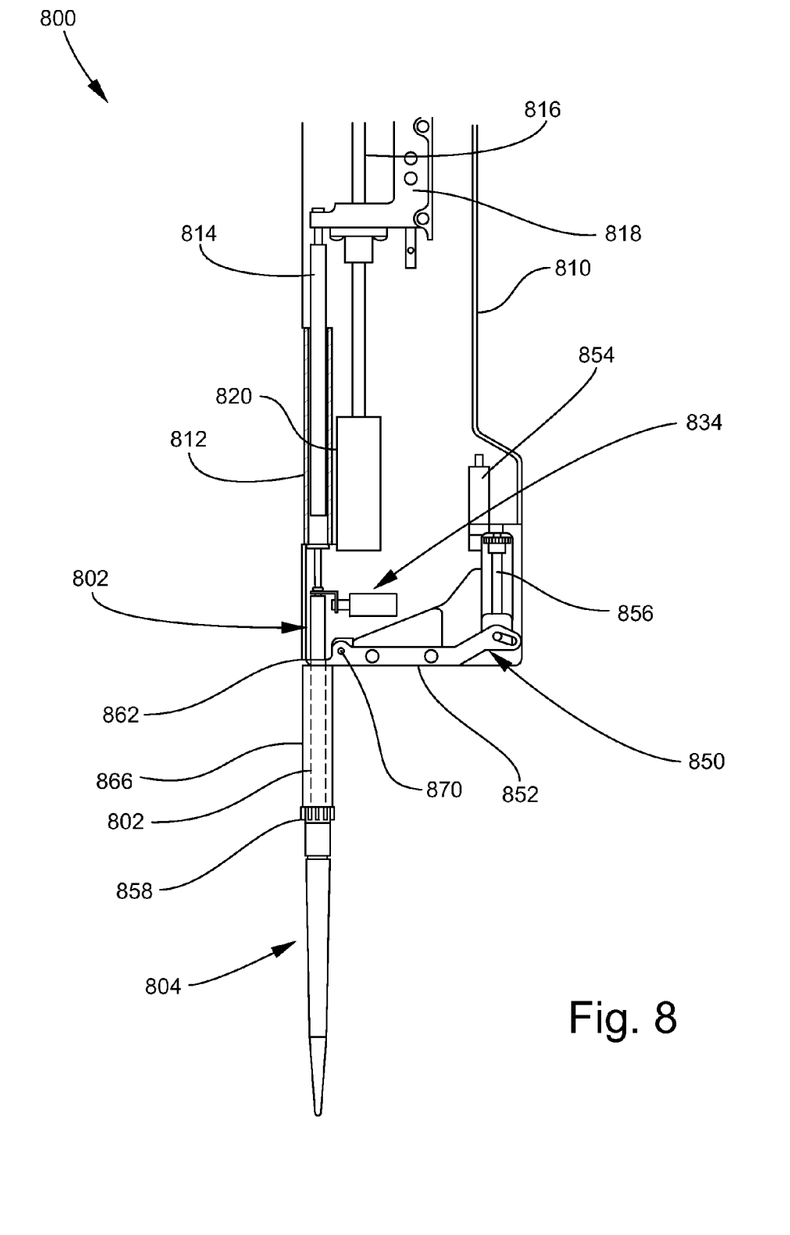
FIG. 8 is an elevation view of an example of an automated pipettor with an adaptor and pipette tip loaded thereon according to some embodiments.
Figure 9:
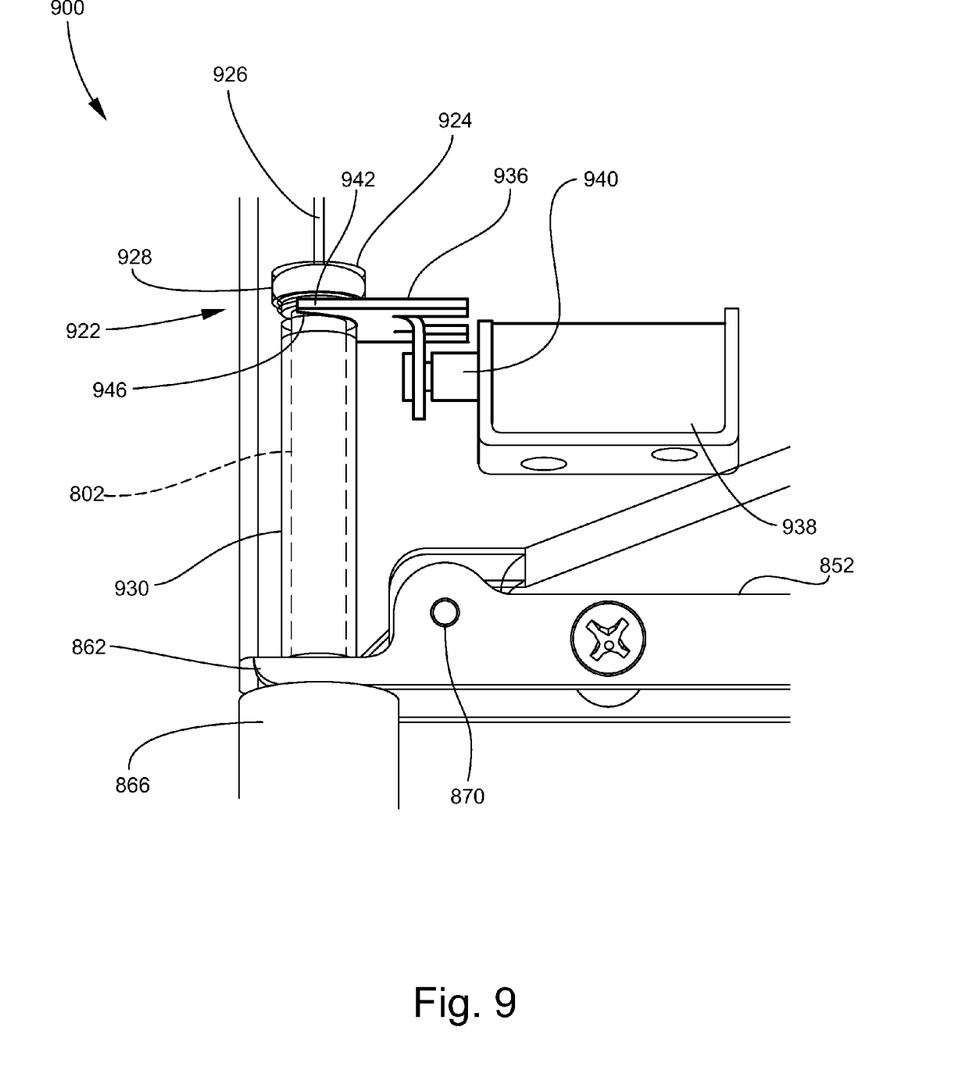
FIG. 9 is a detailed elevation view of a section of the pipettor illustrated in FIG. 8 at which the pipettor interfaces with the adaptor.

FIG. 8 is an elevation view of an example of a syringe-based pipettor 800 with an adaptor 802 and pipette tip 804 loaded thereon. FIG. 9 is a detailed elevation view of a section of the pipettor 800 where it interfaces with the adaptor 802. One or more pipettors 800 may be part of the movable pipettor head of a liquid handling apparatus as described above. The pipettor 800 may generally include a housing 810 and various structural members supporting components of the pipettor 800. The pipettor 800 includes a syringe barrel 812 in which a piston 814 translates to alternately create a vacuum when aspirating liquid into the pipette tip 804 and positive pressure when dispensing liquid from the pipette tip 804. The piston 814 may be driven by a lead screw 816 and associated linkages 818, which in turn may be driven by a bi-directional motor 820. In this embodiment, as best shown in FIG. 9, a proximal end 922 of the adaptor 802 is inserted in a receptacle 924 (e.g., a cylindrical recess or socket) in the housing 810. The receptacle 924 is in fluid communication with the syringe barrel 812 via a passage 926. A sealing element 928 such as an o-ring may be provided in the receptacle 924 to enhance the fluid-tight sealing interface between the adaptor 802 and the syringe barrel 812. The adaptor 802 may be inserted through an opening at the bottom of the housing 810 and through a bore 930 in the housing 810 that leads to the receptacle 924. The inside diameter of the bore 930 may be slightly greater than the outside diameter of the adaptor 802 to assist in aligning the adaptor 802 with the receptacle 924 and aligning the adaptor 802 so that its distal end is consistently placed for interfacing to tips and plates, etc.

The pipettor 800 may further include a locking mechanism 834 configured to lock the adaptor 802 in a sealing position with the pipettor 800. As best shown in FIG. 9, the locking mechanism 834 may include a bar 936 configured to engage the adaptor 802, and an actuator 938 mechanically communicating with the bar 936 either directly or through a linkage 940. The actuator 938 is configured to move the bar 936 alternately between an extended or locking position and a retracted or released position. At the locking position, the bar 936 holds the adaptor 802 in a seated position in the receptacle 924 such that a fluid-tight air path is established between the syringe barrel 812 (and passage 926) and the bore of the adaptor 802. At the released position, the bar 936 is disengaged from the adaptor 802 to allow the adaptor 802 to be freely removed from the syringe housing 810. In the embodiment specifically illustrated, the bar 936 is configured as a yoke, terminating at two fingers 942. The fingers 942 are spaced apart from each other so that they can move into the space defined by a circumferential groove 946 of the adaptor proximal end 922. In the locked position, the fingers 942 prevent the adaptor 802 from moving vertically downward, and may or may not exert an upward force on the adaptor 802 to enhance the seating of the adaptor 802 against the surface of the receptacle 924. Also in the embodiment specifically illustrated, the actuator 938 is a solenoid and the linkage 940 is a plunger actuated by the solenoid. In other embodiments the actuator 938 may be or include, for example, a stepper motor, a pneumatic cylinder, a shape memory alloy (e.g., nickel-titanium or "nitinol"), etc. The actuator 938 or linkage 940 may be spring-biased toward the locking position.

The pipettor 800 is compatible with a reusable pipette tip that is usable without the adaptor 802. In this case, the reusable pipette tip is inserted through the tube 930 and seated in the receptacle 924. As noted above, the proximal end of the reusable pipette tip has the same configuration as that of the adaptor 802. Thus, the locking mechanism 834 may be utilized to lock the reusable pipette tip in place and thereafter release it, in the manner described above.

The pipettor 800 may further include an ejection mechanism 850 configured to eject the (disposable) pipette tip 804 from the adaptor 802. The ejection mechanism 850 may include an arm or lever 852 configured to engage the pipette tip 804, and an actuator 854 mechanically communicating with the lever 852 either directly or through a linkage 856. The actuator 854 is configured to move the lever 852 alternately between a non-ejecting position and an ejecting position. In moving toward the ejecting position, the actuator 854 moves the lever 852 in a direction that pushes or pulls the pipette tip 804 away from the adaptor 802 so as to decouple a proximal end 858 of the pipette tip 804 from the adaptor distal end. In the embodiment specifically illustrated and as best shown in FIG. 9, the lever 852 is configured as a yoke, terminating at two spaced-art fingers 862 that straddle the adaptor 802. The fingers 862 may be located at the opening at the bottom of the syringe housing 810. In this embodiment, the lever 852 engages the pipette tip 804 indirectly through the use of a sleeve 866 surrounding a portion of the adaptor 802. The axial length of the sleeve 866 may be selected such that, when the adaptor 802 and pipette tip 804 are coupled to the pipettor 800, the sleeve 866 is positioned between the fingers 862 and the pipette tip proximal end 858. In this embodiment, the outer diameter of the pipette tip proximal end 858 is greater than that of the adaptor distal end. The sleeve 866 may, for example, be initially provided on the adaptor 802 when the adaptor 802 is stored in an adaptor holder on the deck of the associated liquid handling apparatus. The sleeve 866 may be supported on the adaptor 802 by any suitable means, such as by resting on an annular shoulder or collar protruding in a radial direction outward from the outer surface of the adaptor 802, by means of a pin that extends through the wall of the sleeve 866 into contact with the outer surface of the adaptor 802, etc. The actuator 854 may be a solenoid or any other type of actuator such as those noted above. The actuator 854 or linkage 856 may be spring-biased toward the non-ejecting position.

To eject the pipette tip 804 from the adaptor 802, the actuator 854 drives the linkage 856 in a direction that causes the linkage 856 to rotate the lever 852 about a pivot 870 (counterclockwise from the perspective of FIGS. 8 and 9). This rotation causes the fingers 862 to bear down on the sleeve 866, and the sleeve 866 in turn to bear down on the pipette tip 804, thereby pushing the pipette tip 804 off of the adaptor 802.

An example of a method for operating a pipettor will now be described with reference made primarily to FIGS. 1, 2, 4, 8 and 9. Initially, different pipette tips and corresponding adaptors may be loaded on the deck 104 (FIG. 1) of the liquid handling apparatus 100. For example, first (disposable) pipette tips 412, second (disposable) pipette tips 418 and reusable pipette tips 410 (FIG. 4) may be provided on one or more of the first pipette tip holder 202, second pipette tip holder 204 and third pipette tip holder 206 (FIG. 2). Also, first adaptors 432 and second adaptors 438 (FIG. 4) may be provided on one or more of the first adaptor holder 208 and second adaptor holder 210 (FIG. 2). The locations of the holders 202, 204, 206, 208 and 210 (and other deck components to be utilized during the method) may be stored in a memory associated with the controller 120 so that the controller 120 can instruct the pipetting device 108 to move to the correct deck sites at appropriate times during the method. Locations and other information regarding deck components may be acquired, for example, by reading bar codes or RFID tags as appreciated by persons skilled in the art.

Pipette tips of a certain size or type, for example the first pipette tips 412, are selected for operation with the pipetting device 108. The selection may, for example, be done by the user inputting the selection into the a control panel of the liquid handling apparatus 100, or by initiating a program executed by the controller 120 that performs the selection at the appropriate time. The first pipette tips 412 may then be fluidly coupled to the pipettors 800 of the pipetting device 108 as follows. The pipetting device 108 is driven to move to a position above, for example, the first adaptor holder 208 at which the receptacles 924 of the pipettors 800 (FIGS. 8 and 9) are aligned with the corresponding proximal ends of the first adaptors 432 held in the first adaptor holder 208. The pipettors 800 are then lowered until the first adaptors 432 are inserted through the corresponding openings and bores 930 of the pipettors 800 and become seated in the corresponding receptacles 924. The locking mechanisms 834 of the pipettors 800 are then actuated to lock the first adaptors 432 in place as described above. With the first adaptors 432 so installed, the pipettors 800 are then raised and the pipetting device 108 is moved to a position above, for example, the first pipette tip holder 202 at which the distal ends of the first adaptors 432 are aligned with the corresponding proximal ends of first pipette tips 412 held in the first pipette tip holder 202. The pipettors 800 are then lowered until the first adaptors 432 are fluidly coupled with the first pipette tips 412 as described above.

With the first pipette tips 412 so installed, the pipettors 800 are raised and the pipetting device 108 is ready to carry out pipetting operations called for by the method. For example, the pipetting device 108 may be moved to and aligned with one of the liquid containers 214, 216, and 218 provided on the deck 104, and the pipettors 800 then lowered as necessary to enable them to be operated to aspirate liquid from selected wells, vials, or the like of the selected liquid container 214, 216, and 218, and into the respective first pipette tips 412. The pipetting device 108 may then be moved to and aligned with another liquid container 214, 216, and 218, and the pipettors 800 then lowered as necessary to enable them to be operated to dispense liquid from the first pipette tips 412 into the selected wells, vials, etc. of this liquid container 214, 216, and 218. At this point, any further liquid handling operations may be implemented as called for by the method. For example, the liquid container 214, 216, and 218 containing the dispensed amounts of liquid may be picked up by the robot 114 and transported to an off-deck location, such as another liquid handling apparatus, an analytical instrument, etc.

After the first pipette tips 412 have been used, they may be discarded in an automated manner. The first pipette tips 412 are first decoupled from the pipettors 800, which may be done as follows. The pipettor 108 is moved to a location on the deck 104 designated for collecting used pipette tips. The ejection mechanisms 850 of the pipettors 800 are then actuated to eject the first pipette tips 412 from the first adaptors 432 as described above. A set of fresh first pipette tips 412 located on the deck 104 may then be coupled with first adaptors 432 if desired. Generally, the first adaptors 432 do not need to be cleaned as they do not come into contact with the liquids being handled; however, they may be cleaned or replaced as necessary.

Alternatively, the method may entail exchanging the first pipette tips 412 with a different type or size of pipette tips, e.g., the second pipette tips 418, which may be done as follows. After decoupling the first pipette tips 412, the pipetting device 108 is moved to and aligned with the first adaptor holder 208. The pipettors 800 are then lowered until the first adaptors 432 are inserted through the respective apertures 218 of the first adaptor holder 208 and are securely retained in apertures 218 by a press-fitted interface or other mechanism. The locking mechanisms 834 of the pipettors 800 are then actuated to release the first adaptors 432 as described above. The pipettors 800 are then raised, leaving the first adaptors 432 retained in the first adaptor holder 208. The pipetting device 108 is then moved to the second adaptor holder 210 to fluidly couple the second adaptors 438 with the pipettors 800, and then moved to the second pipette tip holder 204 to fluidly couple the second pipette tips 418 with the second adaptors 438, in the manner described above. The pipetting device 108 is then ready for pipetting operations employing the second pipette tips 418. Alternatively, as described above the first adaptor holder 208 may also hold second adaptors 438, in which case the pipetting device 108 may not need to be moved to a different adaptor holder such as the second adaptor holder 210. Also, the first pipette tip holder 202 may also hold second pipette tips 418, in which case the pipetting device 108 may not need to be moved to a different pipette tip holder such as the second pipette tip holder 204.

As a further alternative, in an embodiment in which the same adaptor holder holds adaptors of different interface geometries, the same pipetting device may be utilized to couple pipette tips of different sizes to matching adaptors installed on different pipettors 800, thus allowing pipette tips of different sizes to be employed simultaneously with the same pipetting device, without requiring any modification to the pipetting device.

The method may be repeated any number of times to exchange and utilize different sizes or types of pipette tips, including different sizes of reusable pipette tips 410. After using reusable pipette tips 410, the pipetting device 108 may be moved to a rinse station located on the deck 104, or the robot 114 may be operated to transport the third pipette tip holder 206 (with the reusable pipette tips 410 carried thereon) to an off-deck rinse station.

The present disclosure also encompasses kits for use with a pipettor. In some embodiments, a kit may include a set of disposable or reusable pipette tips of the same size, or a combination of pipette tips of different sizes and/or types. In other embodiments, a kit may include a set of adaptors of the same size, or a combination of adaptors of different sizes. In other embodiments, a kit may include a set of disposable pipette tips and also a set of adaptors matched to the geometry of these pipette tips. A kit that includes adaptors may also include sleeves (e.g., the sleeves 866 shown in FIGS. 8 and 9) for the adaptors. The sleeves may be pre-installed on the adaptors or provided separately in the same container of the kit. In any of the foregoing embodiments, the kit may include a suitable container for containing the pipetting components (pipette tips, adaptors, sleeves, etc.), and may also include instructions for use. In any of the foregoing embodiments, the kit may include holders for the pipetting components. The holders may be configured for immediate use on the deck of a liquid handling apparatus, and may be of a standard size or format directly compatible with an existing pipettor (and robot, if applicable). In any of the foregoing embodiments, the kit may be provided to a user separately from a pipetting device or liquid handling system, or may be provided with a pipetting device or liquid handling system.

It will be understood that one or more of the processes, sub-processes, and process steps described herein may be performed by hardware, firmware, software, or a combination of two or more of the foregoing, on one or more electronic or digitally-controlled devices. The software may reside in a software memory (not shown) in a suitable electronic processing component or system such as, for example, the system controller 120 schematically depicted in FIG. 1. The software memory may include an ordered listing of executable instructions for implementing logical functions (that is, "logic" that may be implemented in digital form such as digital circuitry or source code, or in analog form such as an analog source such as an analog electrical, sound, or video signal). The instructions may be executed within a processing module, which includes, for example, one or more microprocessors, general purpose processors, combinations of processors, digital signal processors (DSPs), or application specific integrated circuits (ASICs). Further, the schematic diagrams describe a logical division of functions having physical (hardware and/or software) implementations that are not limited by architecture or the physical layout of the functions. The examples of systems described herein may be implemented in a variety of configurations and operate as hardware/software components in a single hardware/software unit, or in separate hardware/software units.

The executable instructions may be implemented as a computer program product having instructions stored therein which, when executed by a processing module of an electronic system (e.g., the system controller 120 in FIG. 1), direct the electronic system to carry out the instructions. The computer program product may be selectively embodied in any non-transitory computer-readable storage medium for use by or in connection with an instruction execution system, apparatus, or device, such as a electronic computer-based system, processor-containing system, or other system that may selectively fetch the instructions from the instruction execution system, apparatus, or device and execute the instructions. In the context of this disclosure, a computer-readable storage medium is any non-transitory means that may store the program for use by or in connection with the instruction execution system, apparatus, or device. The non-transitory computer-readable storage medium may selectively be, for example, an electronic, magnetic, optical, electromagnetic, infrared, or semiconductor system, apparatus, or device. A non-exhaustive list of more specific examples of non-transitory computer readable media include: an electrical connection having one or more wires (electronic); a portable computer diskette (magnetic); a random access memory (electronic); a read-only memory (electronic); an erasable programmable read only memory such as, for example, flash memory (electronic); a compact disc memory such as, for example, CD-ROM, CD-R, CD-RW (optical); and digital versatile disc memory, i.e., DVD (optical). Note that the non-transitory computer-readable storage medium may even be paper or another suitable medium upon which the program is printed, as the program can be electronically captured via, for instance, optical scanning of the paper or other medium, then compiled, interpreted, or otherwise processed in a suitable manner if necessary, and then stored in a computer memory or machine memory.

It will also be understood that the term "in signal communication" as used herein means that two or more systems, devices, components, modules, or sub-modules are capable of communicating with each other via signals that travel over some type of signal path. The signals may be communication, power, data, or energy signals, which may communicate information, power, or energy from a first system, device, component, module, or sub-module to a second system, device, component, module, or sub-module along a signal path between the first and second system, device, component, module, or sub-module. The signal paths may include physical, electrical, magnetic, electromagnetic, electrochemical, optical, wired, or wireless connections. The signal paths may also include additional systems, devices, components, modules, or sub-modules between the first and second system, device, component, module, or sub-module.

More generally, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A method for operating a pipettor, the method comprising:
   selecting a first pipette tip from a plurality of pipette tips, the plurality of pipette tips comprising one or more of the first pipette tips and one or more second pipette tips, wherein the first pipette tip comprises a first pipette tip proximal end of a first interface geometry and the second pipette tip comprises a second pipette tip proximal end of a second interface geometry different from the first interface geometry;
   selecting a first adaptor from a plurality of hollow adaptors, the plurality of adaptors comprising one or more of the first adaptors and one or more second adaptors, wherein the first adaptor comprises a first adaptor proximal end and a first adaptor distal end, the first adaptor distal end is configured for interfacing with the first pipette tip proximal end, the second adaptor comprises a second adaptor proximal end of a same interface geometry as the first adaptor proximal end and a second adaptor distal end of a different interface geometry than the first adaptor distal end, and the second adaptor distal end is configured for interfacing with the second pipette tip proximal end;
   moving the pipettor to the selected first adaptor;
   fluidly coupling the pipettor with the first adaptor;
   moving the pipettor with the first adaptor to the selected first pipette tip; and
   fluidly coupling the first adaptor with the first pipette tip.

2. The method of claim 1, wherein fluidly coupling the pipettor with the first adaptor comprises moving the pipettor into secure contact with the first adaptor proximal end.

3. The method of claim 2, wherein fluidly coupling the pipettor with the first adaptor comprises locking the first adaptor in a sealed position at which the first adaptor proximal end abuts a surface of the pipettor.

4. The method of claim 3, wherein locking comprises actuating a bar of the pipettor into engagement with the first adaptor, and wherein the engagement holds the first adaptor in the sealed position.

5. The method of claim 1, wherein fluidly coupling the first adaptor with the first pipette tip comprises moving the first adaptor distal end into secure contact with the first pipette tip proximal end.

6. The method of claim 5, wherein fluidly coupling the first adaptor with the first pipette tip comprises lowering the adaptor until the first adaptor distal end is press fitted to the first pipette tip proximal end.

7. The method of claim 6, comprising, after fluidly coupling the first adaptor with the first pipette tip, decoupling the first pipette tip from the first adaptor by actuating a lever of the pipettor in a direction that forcibly ejects the first pipette tip proximal end from the first adaptor distal end.

8. The method of claim 1, wherein the pipettor is part of a liquid handling apparatus comprising a deck, the one or more first pipette tips and second pipette tips are held by at least one pipette tip holder disposed on the deck, the one or more first adaptors and second adaptors are held by at least one adaptor holder disposed on the deck, moving the pipettor to the selected first adaptor comprises moving the pipettor to the at least one adaptor holder, and moving the pipettor to the selected first pipette tip comprises moving the pipettor to at least one pipette tip holder.

9. The method of claim 1, wherein the pipettor is part of a liquid handling apparatus comprising a deck, and further comprising, after fluidly coupling the first adaptor with the first pipette tip, performing a pipetting operation selected from the group consisting of:
   moving the pipettor to a container disposed on the deck and aspirating liquid from the container into the first pipette tip;
   moving the pipettor to a container disposed on the deck and aspirating liquid from the container into the first pipette tip, followed by operating a robot to move the container to a site external to the deck; and
   moving the pipettor to a first container disposed on the deck and aspirating liquid from the first container into the first pipette tip, followed by moving the pipettor to a second container disposed on the deck and dispensing the liquid from the first pipette tip into the second container.

10. The method of claim 1, comprising decoupling the first adaptor from the pipettor, selecting a second pipette tip from the plurality of pipette tips, selecting a second adaptor from the plurality of adaptors, moving the pipettor to the selected second adaptor, fluidly coupling the pipettor with the second adaptor, moving the pipettor with the second adaptor to the selected second pipette tip, and fluidly coupling the second adaptor with the second pipette tip.

11. The method of claim 1, comprising decoupling the first adaptor from the pipettor, moving the pipettor to a reusable pipette tip comprising a reusable pipette tip proximal end of the same interface geometry as the first adaptor proximal end and the second adaptor proximal end, and fluidly coupling the pipettor directly with the reusable pipette tip.

12. The method of claim 1, comprising, after fluidly coupling the pipettor with the first adaptor, moving the pipettor to an adaptor holder, lowering the pipettor until an outer surface of the first adaptor is press fitted to an aperture of the adaptor holder, decoupling the first adaptor from the pipettor, and raising the pipettor wherein the first adaptor is separated from the pipettor and retained in the aperture.

13. The method of claim 1, wherein selecting the first pipette tip comprises selecting a plurality of the first pipette tips, selecting the first adaptor comprises selecting a plurality of the first adaptors, fluidly coupling the pipettor with the first adaptor comprises fluidly coupling a plurality of pipettors with the plurality of respective first adaptors simultaneously, and fluidly coupling the first adaptor with the first pipette tip comprises fluidly coupling the plurality of first adaptors with the plurality of respective first pipette tips simultaneously.

* * * * *